United States Patent
Shorter et al.

(10) Patent No.: US 6,206,933 B1
(45) Date of Patent: Mar. 27, 2001

(54) KNEE PROSTHESIS

(75) Inventors: John Jeffrey Shorter, West Sussex (GB); Alan Aulie, Redmond, OR (US)

(73) Assignee: Chas. A. Blatchford & Sons Limited, Basingstoke (GB)

( * ) Notice: Subject to any disclaimer, the term of this patent is extended or adjusted under 35 U.S.C. 154(b) by 0 days.

(21) Appl. No.: 09/043,594

(22) PCT Filed: Sep. 20, 1996

(86) PCT No.: PCT/GB96/02329

§ 371 Date: Jun. 26, 1998

§ 102(e) Date: Jun. 26, 1998

(87) PCT Pub. No.: WO97/10781

PCT Pub. Date: Mar. 27, 1997

(30) Foreign Application Priority Data

Sep. 22, 1995 (GB) .................................... 9519439
Mar. 25, 1996 (GB) .................................... 9606219

(51) Int. Cl.$^7$ ...................................................... A61F 2/64
(52) U.S. Cl. ............................................................. 623/44
(58) Field of Search ................................. 623/44, 45, 41, 623/42, 43

(56) References Cited

U.S. PATENT DOCUMENTS

| | | | |
|---|---|---|---|
| 2,551,537 | * | 5/1951 | Havens ................................... 623/44 |
| 3,666,299 | * | 5/1972 | Butler ..................................... 287/94 |
| 3,694,823 | * | 10/1972 | May ........................................ 623/44 |
| 3,723,997 | * | 4/1973 | Kolman ................................... 623/44 |
| 3,934,273 | * | 1/1976 | Mortensen .............................. 623/44 |
| 3,982,279 | * | 9/1976 | Valenti et al. .......................... 623/44 |
| 4,206,519 | * | 6/1980 | Blatchford et al. .................... 623/44 |

FOREIGN PATENT DOCUMENTS

| | | | |
|---|---|---|---|
| 2023040 | * | 8/1971 | (DE) . |
| 2161386 | * | 1/1986 | (GB) .................................... 623/44 |

OTHER PUBLICATIONS

Orthopaedic Appliances Atlas, vol. 2—Artificial Limps, J.W Edwards, 1960.*

* cited by examiner

*Primary Examiner*—Bruce Snow
(74) *Attorney, Agent, or Firm*—Barnes & Thornburg

(57) ABSTRACT

An artificial knee comprises first and second pivotally interconnected knee components and first and second interengaging brake components for locking the knee components together. The first and second brake components are associated respectively with the first and second knee components, respectively. The second brake component is made of a resiliently deformable material. The arrangement is such that, when the artificial knee is subjected to a first load condition, the brake components are substantially free to slide against one another, and when the artificial knee is under a second, higher load condition, the second brake component is resiliently deformed against the first brake component to lock the two brake components together, thereby locking the two knee components together. The first and second brake components are provided with interengaging surfaces which are inclined to the axis about which the two knee components are pivoted, and the first and second brake components constitute the pivotal interconnection between the two knee components.

30 Claims, 8 Drawing Sheets

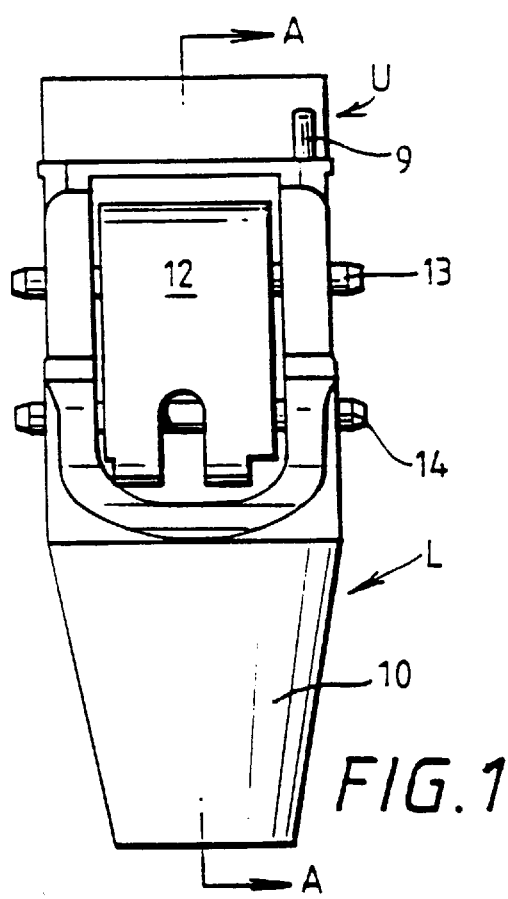
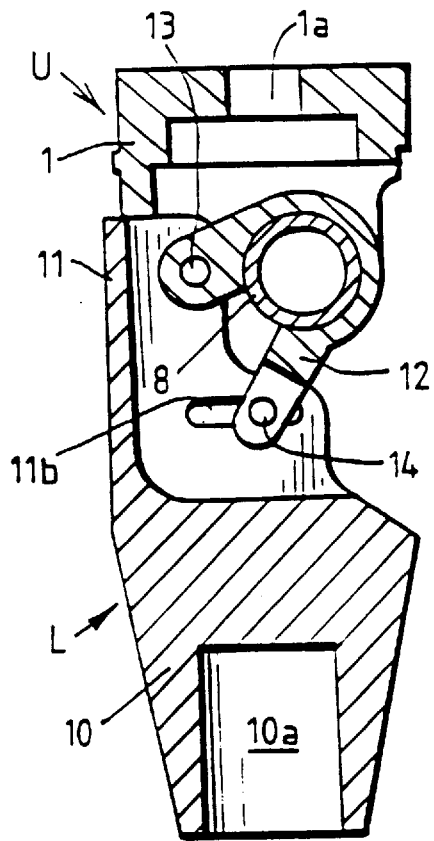
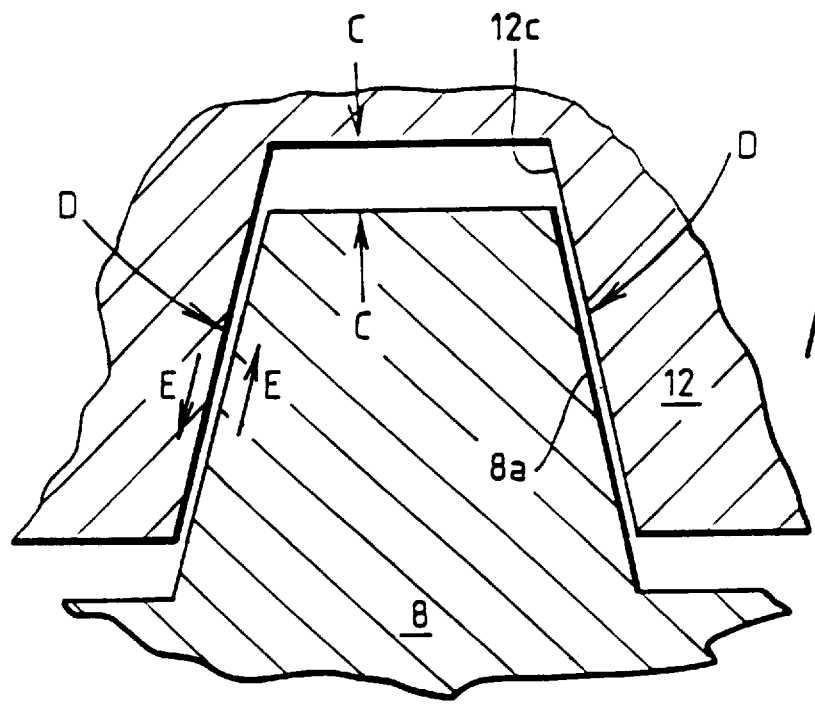

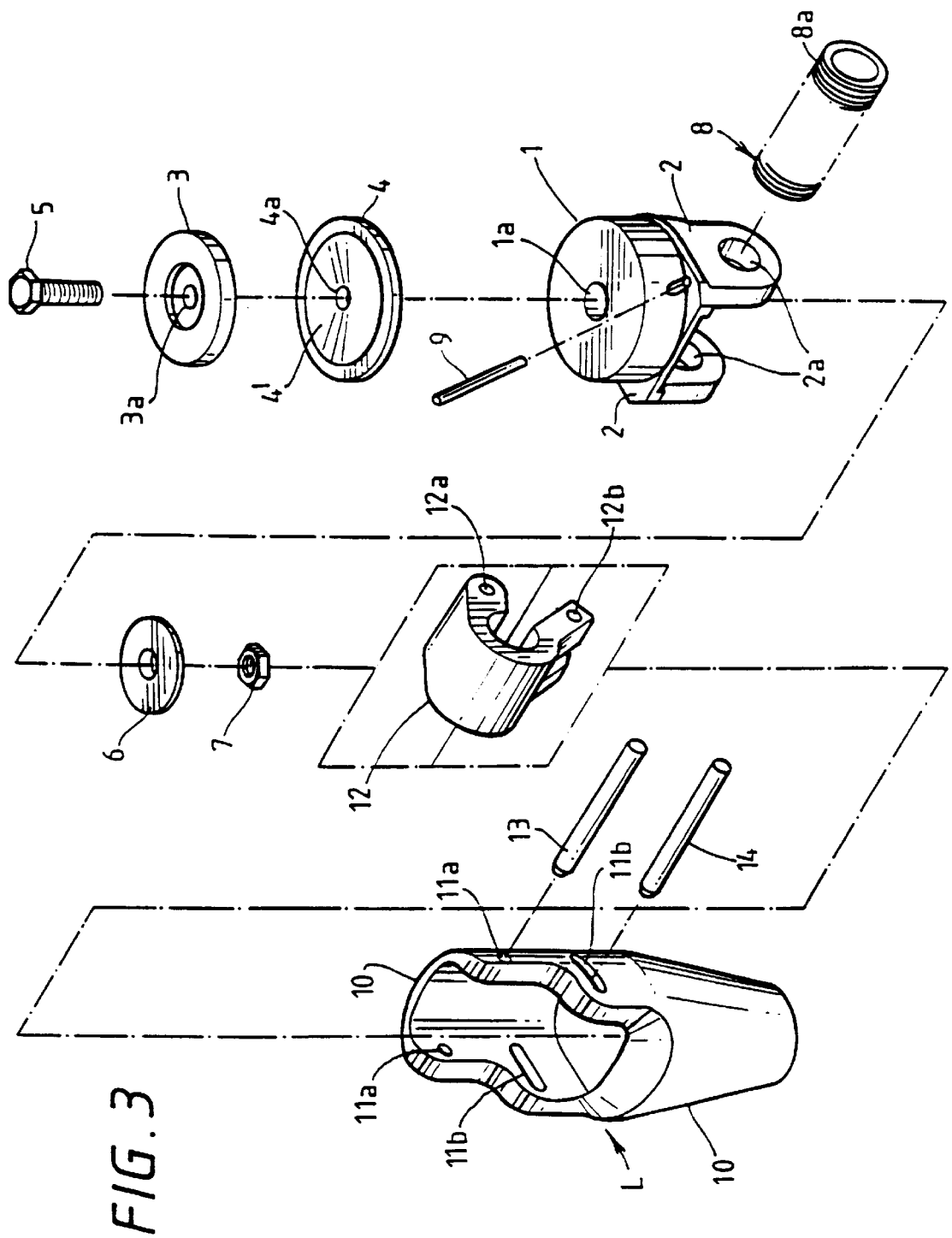

KNEE PROSTHESIS

CROSS-REFERENCES TO RELATED APPLICATIONS

This application is a U.S. national application of international application Ser. No. PCT/GB96/02329 filed Sep. 20, 1996, which claims priority to British Serial Nos. 9519439.5 and 9606219.5 filed Sep. 22, 1995 and Mar. 25, 1996, respectively.

This invention relates to a knee prosthesis.

It is usual for a leg amputee to wear a prosthesis in order to provide the wearer with improved mobility. Such a prothesis should be comfortable to wear, and should simulate the natural movement of the replaced limb.

A known knee prosthesis includes a pair of split collars pivotally attached, in use, to a thigh member and a shin member respectively. One of the collars carries a brake drum, around which a brake band passes. In use, as the knee is loaded, an actuating lever engages the brake band to tighten it against the brake drum, thereby locking the knee in any desired position. The disadvantage of this known artificial knee is that it requires the use of machined elements, and so is relatively expensive.

The aim of the invention is to provide an improved form of artificial knee.

The present invention provides an artificial knee comprising first and second pivotally interconnected knee components, and first and second interengaging brake components for locking the knee components together, the first and second brake components being associated respectively with the first and second knee components, wherein one of the brake components is made of a resiliently deformable material, and the arrangement is such that, when the artificial knee is subjected to a first load condition, the brake components are substantially free to slide against one another, and, when the artificial knee is under a second, higher load condition, said one brake component is resiliently deformed against the other brake component to lock the two brake components together, thereby locking the two knee components together, wherein the first and second brake components are provided with interengaging surfaces which are inclined to the axis about which the two knee components are pivoted, and the first and second brake components constitute the pivotal interconnection between the two knee components.

As the brake components constitute the pivotal interconnection between the two knee components, they also constitute a load/weight bearing for the artificial knee, thereby reducing the number of components needed to make the knee, leading to a cost reduction.

Generally speaking, the first load condition is when the artificial knee is subjected to substantially no axial load; and the second load condition is when the knee is subjected to a weight-bearing axial load.

Preferably, the first brake component is separate from, and supported by, the first knee component; and the second brake component is separate from, and supported by, the second knee component.

Advantageously, the artificial knee further comprises means for preventing rotation of the first brake component relative to the first knee component.

Conveniently, the first and second brake components are inner and outer brake members, the outer brake member being rotatable about the inner brake member about the axis of rotation of the knee. Thus, when the knee is subjected to an actuating load, the outer brake member grips the inner brake member.

Thus, for example, the brake components may be a shaft defining the knee axis and secured to one of the knee components, and a clamp substantially encircling the shaft and secured to the other of the knee components, with the shaft and clamp having an interengaging rib and groove of complementary wedge-shaped cross-section. The rib and groove are in sliding engagement with each other in the first load condition when the knee components are rotated with respect to each other, and grip each other to resist such rotation when the clamp is tightened around the shaft in response to the second load condition.

Advantageously, the brake components have, respectively, a projection outwardly tapered in cross-section, and a recess which receives the projection and is of complementary shape. Thus, on application of an actuating load, the projection is urged into the recess to engage the recess surfaces in a wedging action.

Preferably, the first brake component is an externally screw-threaded member, the flanks of the threads being inclined to the pivot axis. Conveniently, the first brake component is provided with an acme screw thread, and is made of a generally rigid (non-resiliently deformable) material such as stainless steel or aluminium alloy.

In a preferred embodiment, the second brake component has a base portion and a pair of arms, the internal surface of the base portion being rounded and being provided with an internal screw thread which complements the external screw thread of the first brake component. The second brake component may be said one brake component, and said resiliently deformable material may be a plastics material such as nylon 6,6.

Advantageously, the free ends of the arms of the second brake component are connected to the second knee component by first and second pins. Preferably, the second knee component defines a pair of supports between which the second brake component is mounted, the first pin passes through aligned circular apertures in the supports and through a circular aperture in one of the arms of the second brake component, and the second pin passes through aligned apertures in the supports and through an aperture in the other arm of the second brake component.

In a preferred embodiment, the second pin passes through aligned elongate apertures in the supports and through a circular apertures in said other arm. In this case, the apertures in the supports may be so positioned that, when the artificial knee is subjected to the second load condition, the second pin is forced along the elongate apertures in the supports so that the internal screw threads of the rounded base portion of the second brake component are forced against the external screw threads of the first brake component, thereby locking the two brake components together. Moreover, as the second pin is forced along the elongate apertures in the supports, the distance between the two pins decreases, and this leads to "hoop stress" in the second brake component, thereby increasing the force locking the two brake components together. This "hoop stress" is increased by the flexion moment and the friction between the two brake components.

Advantageously, the circular aperture in said other arm of the second brake component is more remote from the second knee component than the circular aperture in said one arm of the second brake component. Preferably, the free ends of the arms of the second brake component are directed towards the anterior of the knee.

In a preferred embodiment, said other arm of the second brake component is tangential to the hyper-extension moment when the knee is in hyper-extension. This leads to the hyper-extension moment being resisted by the second pin, so that the second brake component is subjected only to tension fores. Conveniently, the fulcrum of the hyper-extension moment is constituted by an abutment between portions of the two knee components, the abutment being anterior to the knee axis of rotation, and being on the side of said axis remote from the free end of said other arm of the second brake component.

In another preferred embodiment, the second pin passes through aligned circular apertures in the supports and through a circular aperture in said other arm. In this case, the apertures in the supports and the apertures in the arms of the second brake component may be positioned such that the first and second pins are substantially aligned with the axis about which the two knee components are pivoted.

The artificial knee may further comprise means, such as a threaded pin, for pre-tensioning the arms of the second brake component towards one another. This enables the artificial knee to be adjusted to suit amputees of different body weights.

Where the second pin passes through circular apertures in the supports, the pre-tensioning means may be constituted by a pin member associated with said one arm, an abutment member associated with said other arm, and a spring acting to bias the two arms apart, the pin member being fixed to the abutment member in such a manner as to permit relative movement therebetween. The free end of the pin member may threadingly engage the abutment member, and the pin member may be supported by an externally-threaded sleeve mounted in a threaded counter-bore formed in said one arm. Advantageously, the spring acts between said other arm and the sleeve.

Preferably, the abutment member is a clevis having an apertured end through which the second pin passes, the engagement between the second pin and the clevis and the engagement of the second pin with the aperture in said other arm constituting means for fixing the abutment member to said other arm.

Advantageously, the second brake component is a resilient deformable loop which can be tensioned around the first brake component by an actuating load.

Preferably, the second brake component is a generally V-shaped member, the base of the "V" constituting the base portion of the second brake component.

Alternatively, the second brake component is a generally C-shaped member. In this case, the base portion of the C-shaped second brake component may be formed with an arcuate slot. Advantageously, the first knee component defines a pair of spaced support members between which the first brake component is mounted, the artificial knee further comprising a stop pin passing through aligned apertures in the support members and through the arcuate slot in the second brake component, the arrangement being such that pivotal movement between the two brake components is limited by engagement of the stop pin with the ends of the arcuate slot.

Conveniently, the artificial knee further comprises a tubular stop member positioned within the arcuate slot and closely surrounding the stop pin.

The rotation-preventing means may be constituted by a pair of torque arms non-rotatably mounted in apertures formed in the support means, the torque arms being formed with inwardly-extending projections which mate with complementary slots formed in the adjacent ends of the first brake component.

Advantageously, the rotation-preventing means further comprises a threaded pin for clamping the two torque arms firmly in their respective apertures.

Alternatively, the second brake component is generally D-shaped member, said one arm forming part of the upright of the D, and said other arm forming the curved part of the D.

Preferably, the two brake components constitute bearings for the two knee components and means for preventing end-play of the two knee components.

The invention further provides an artificial knee comprising first and second pivotally interconnected knee components, and first and second interengaging brake components for locking the knee components together, the first and second brake components being associated respectively with the first and second knee components, the arrangement being such that, when the artificial knee is subjected to a first load condition, the brake components are substantially free to slide against one another, and, when the artificial knee is under a second, higher load condition, the two brake components are locked together, thereby locking the two knee components together, wherein one of the brake components at least partially surrounds the other brake component, said one brake component having an external surface that is curved in the anterior/posterior plane of the knee and forms an exposed outer anterior surface of the knee in the flexed condition.

This curved external surface gives the artificial knee a good cosmetic appearance.

The invention still further provides an artificial knee comprising first and second pivotally interconnected knee components, and first and second interengaging brake components for locking the knee components together, the first and second brake components being associated respectively with the first and second knee components, wherein one of the brake components is made of a resiliently deformable material, and the arrangement is such that, when the artificial knee is subjected to a first load condition, the brake components are substantially free to slide against one another, and, when the artificial knee is under a second, higher load condition, said one brake component is resiliently deformed against the other brake component to lock the two brake components together, thereby locking the two knee components together, wherein the first and second brake components are provided with interengaging surfaces which are inclined to the axis about which the two knee components are pivoted, said one brake component at least partially surrounds the other brake component, and the brake components are constructed and mounted such that, under the second load condition, a tangential force is induced in said one brake component thereby causing "hoop stress" in that component.

Preferably the two brake components are such that a rotation-inducing load leads to increased "hoop stress" in said one brake component due to the flexion moment and to the friction between the two brake components.

The invention also provides lower limb prosthesis having a thigh component, a shin component, and a knee joint interconnecting the thigh and shin components, wherein the knee joint comprises first and second brake components associated respectively with the thigh and shin components, one of the brake components being made of a resiliently deformable material, the arrangement being such that, when the prosthesis is in a first load condition, the brake components are substantially free to slide against one another, and, when the prosthesis is in a second load condition, said one brake component is resiliently deformed against the other brake component to resist relative pivoting of the shin component with respect to the thigh component, wherein the first and second brake components are provided with interengaging surfaces which are inclined to the axis about which the two knee components are pivoted.

The invention will now be described in greater detail, by way of example, with reference to the drawings, in which:

FIG. 1 is an end elevation of a first form of prosthetic knee constructed in accordance with the invention;

FIG. 2 is a cross-section taken on the line A—A of FIG. 1;

FIG. 3 is an exploded perspective view of the first form of prosthetic knee;

FIG. 4 is an enlarged scrap view showing the interengagement of two of the parts of the first form of prosthetic knee;

Figure 5:
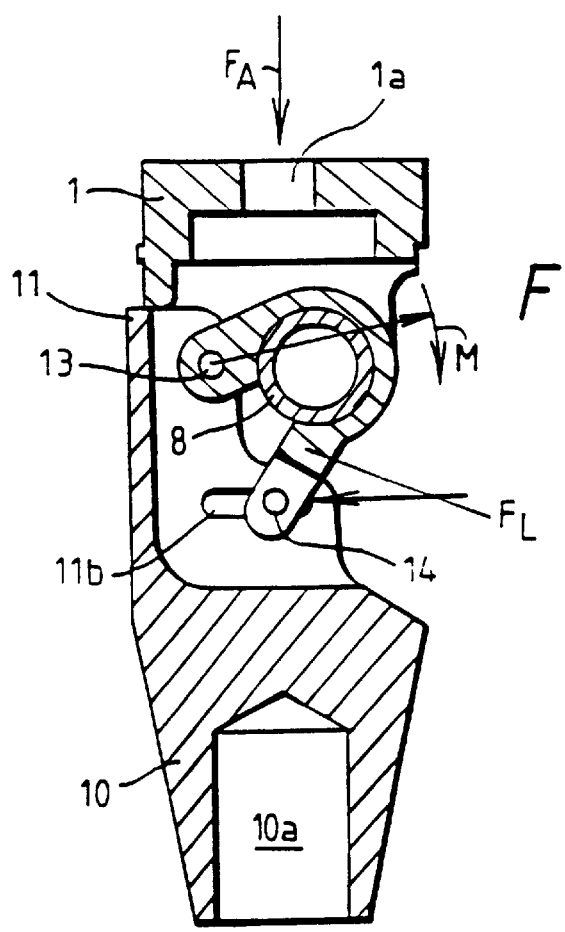
FIG. 5 is a cross-section similar to that of FIG. 2, and showing the effect of axial loads on the first form of prosthetic knee.

Referring to the drawings, FIG. 1 shows a first form of prosthetic knee having upper and lower members, indicated generally by the references U and L, pivotally interconnected in the manner described below. In use, the upper member U is fixed to an above-knee socket (not shown), and the member L is fixed to an artificial shin (not shown).

The upper member U is a one-piece moulded member constituted by a shallow cup-shaped base 1 (see FIGS. 2 and 3) and a pair of integrally-formed, downwardly-depending lugs 2. The base 1 is formed with a circular aperture 1a in its end surface. The upper member 1 is made of an acetal resin such as Delrin (RTM). The lugs 2 are formed with aligned apertures 2a. The base 1 is fixed to the above-knee socket by means of alignment mechanism comprising clamping plates 3 and 4, a bolt 5, a washer 6, and a nut 7 (see FIG. 3). The proximal clamping plate 3 fits inside the socket, and has a convex distal clamping face (not shown) which engages with a complementarily-shaped internal end face of the socket. The distal clamping plate 4 has a concave end surface 4' which complements the external end surface of the socket. In use, the clamping plate 3 is positioned within the socket, and the clamping plate 4 is sandwiched between the socket and the external end face of the base 1. The bolt 5 is then threaded through apertures 3a and 4a in the clamping plates 3 and 4, and through the aperture 1a in the end surface of the base 1. The base 1 can then be fixed to the socket at a selected relative orientation by tightening the nut 7 with the washer 6 positioned against the internal end surface of the base.

An acme screw 8 is supported within the apertures 2a in the lugs 2. The acme screw 8 is made of stainless steel, and is prevented from rotating relative to the lugs by means of a locking pin 9. The screw 8 is formed with an external trapezoidal cross-section acme screw thread 8a having five turns per inch (0.2 inch pitch).

The lower member L is a one-piece moulded member made of an acetal resin such as Delrin (RTM). The member L includes a lower, frusto-conical socket section 10, and an upper, partially cut-away tubular section 11. The upper section 11 is pivotally connected to the upper member U in a manner described below. The lower section 10 includes a socket 10a for receiving an artificial shin. A generally V-shaped brake member 12 is mounted in the upper section 11 of the lower member L by means of a pair of pins 13 and 14. The pin 13 passes through aligned circular apertures 11a in the upper section 11 and through a circular aperture 12a in one leg of the brake member 12. The pin 14 passes through aligned elongate apertures 11b in the section 11, and through a circular aperture 12b in the other leg of the brake member 12. The brake member 12 is made of nylon 6,6, and is formed with an internal acme screw thread 12c (see FIG. 4), which complements the external screw thread 8a of the screw 8. The brake members 8 and 12 thus constitute load-bearing means for pivotally connecting the upper and lower members U and L together.

As shown in FIG. 4, the thread 12c is a sliding fit on the thread 8a when the prosthetic knee is not under load, and there is a clearance between the free end of the thread 8a and the base of the thread 12c (this clearance being indicated by the arrows C). When the brake member 12 is loaded (for example as indicated by the arrows D), the threads 12c and 8a tend to move in the directions of the arrows E, thereby jamming their flanks together and locking the brake member to the screw 8. Although nylon 6,6 running in polished stainless steel produces very low static and dynamic friction, the angle of the interengaging flanks of the threads 8a and 12c produces a total reaction force which is much greater than the radial load on the screw 8, thereby achieving good resistance to torque (and hence good braking) with relatively low applied loads.

FIG. 5 illustrates the forces which provide locking when the knee is subjected to an axial load $F_A$. This load $F_A$ creates a turning moment M centred on the pin 13, and this induces a locking load $F_L$ which forces the pin 14 along the slot 11b (to the left as shown in FIG. 5), and this results in the deformation of the threads 12c of the brake member 12 into locking engagement with the threads 8a of the screw 8. As the brake member 12 is made of a plastics material which has self-lubricating properties and resilience, the threads 12c can slide relative to the threads 8a when the knee is unloaded, so that the knee has good pivotal properties when unloaded and good braking properties when loaded. Moreover, the zero-fit threads 12c and 8a serve to locate the pivoting members of the knee, and prevent play on all axes.

Figure 6:
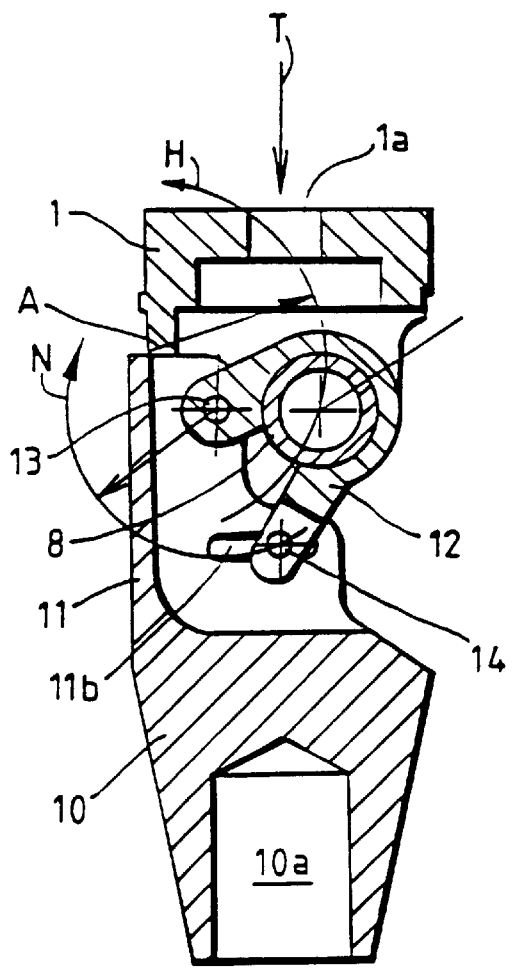
FIG. 6 is a view similar to that of FIG. 2, and showing the effect of hyper-extension forces on the first form of prosthetic knee.

FIG. 6 illustrates the way in which the brake member 12 translates hyper-extension forces into tension loads, thereby absorbing hyper-extension loads in a favourable manner. Thus, when the knee is in hyper-extension, the abutment A between the upper end lower members U and L serves as a fulcrum for the hyper-extension moment H, which is resisted by the pin 14, the lower leg of the brake member 12 being generally tangential to the moment H distally of the knee axis. This results in the low-strength material of the brake member 12 being subjected only to tension forces, thereby minimising bending moments about the axis of the brake member. It should be noted that a trigger load T results in increased "hoop stress" as the distance between the pins 13 and 14 decreases as the pin 14 is forced along the slot 11b (to the left as shown in FIG. 6), the slot not being tangential to the moment line N. Here again, therefore, the tension in the brake member 12 results in the deformation of the threads 12c to jam against the threads 8a, thereby locking the brake member against the screw 8. This braking action increases rapidly as "wedging" of the threads 12c and 8a locks the screw 8 to the brake member 12, as the pin 14 is driven further along the slots 11b. It should also be noted that there is a rotation-induced increase in the "hoop stress" due to the flexion moment and to the friction between the brake member 12 and the screw 8. This further increases the braking action.

The term "hoop stress" is usually used to describe a circumferential stress generated in a continuous section by an internal or an external pressure, and is generally used in connection with "thin-walled" cylinders. The brake member 12 is basically an open "c"-shape, loaded at its free ends. This may be more accurately modelled as a curved beam in bending, in which case the stress generated within the section would vary from a tensile stress at the outside diameter to a compressive stress at the internal diameter. However, the presence of the acme screw 8 means that the deformation of the brake member 12, and hence the compressive circumferential stress, is limited. This constraint generates pressure at the interface between the brake member 12 and the acme screw 8 which, in turn, supplies the friction required for the braking action. The brake member 12 may, therefore, be thought of as being in constrained bending, where the reaction generated at the acme screw 8 by maintaining the internal diameter of the brake member 12 is used to supply the braking effect. The term "hoop stress" will, however, be used throughout this specification to describe this mechanism.

Figure 7:
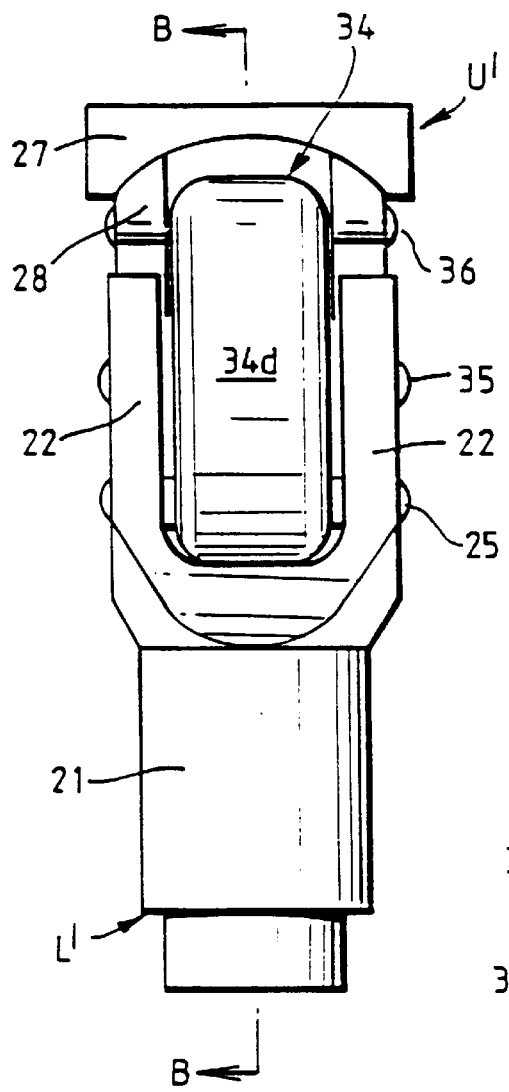
FIG. 7 is an end elevation of a second form of prosthetic knee constructed in accordance with the invention.

FIG. 7 shows a second form of prosthetic knee having upper and lower members, indicated generally by the references U' and L', pivotally interconnected in the manner described below. In use, the upper member U' is fixed to an above-knee socket (not shown), and the member L' is fixed to an artificial shin (not shown).

The lower member L' is constituted by a shallow cup-shaped base 21 (see FIGS. 8 and 9) and a pair of integrally-formed, upwardly-extending lugs 22. The base 21 includes a socket 21a for receiving an artificial shin. The lower member L' is made of an acetal resin such as Delrin (RTM). The lugs 22 are formed with aligned apertures 22a. An acme screw 23 having a thread of trapezoidal cross-section is supported within the apertures 22a in the lugs 22. The acme screw 23 is made of stainless steel, and is prevented from rotating relative to the lugs 22 means of a pair of torque arms 24 mounted in correspondingly-shaped apertures 22b formed in the lugs. The torque arms 24 are each formed with a cross-shaped projection 24a, these projections mating with slots 23a formed in the opposite end faces of the screw 23. A pin 25 passes through apertures 22c formed in the lugs 22, and through apertures 24b in the torque arms 24. The torque arms 24 are fixed to the lugs 22 by a threaded pin 26 which passes through aligned apertures 24c in the torque arms, through the centres of the apertures 22a, and centrally through the screw 23. The screw 23 is formed with an external acme screw thread 23b having five turns per inch (0.2 inch pitch).

The upper member U' is a one-piece moulded member made of an acetal resin such as Delrin (RTM). The member U' includes an upper base plate 27, and an lower partially cut-away tubular section 28. The section 28 is pivotally connected to the lower member L' in manner described below. The base plate 27 is formed with a circular aperture 27a. The base plate 27 is fixed to the above-knee socket by means of an alignment mechanism comprising clamping plates 29 and 30, a bolt 31, a washer 32, and a nut 33 (see FIG. 9). The proximal clamping plate 29 fits inside the socket, and has a convex distal clamping face (not shown) which engages with a complementarily-shaped internal end face of the socket. The distal clamping plate 30 has a concave end surface 30' which complements the external end surface of the socket. In use, the clamping plate 29 is positioned within the socket, and the clamping plate 30 is sandwiched between the socket and the external end face of the base plate 27. The bolt 31 is then threaded through apertures 29a and 30a in the clamping plates 29 and 30, and through the aperture 27a in the end surface of the base plate 27. The base plate 27 can then be fixed to the socket at a selected orientation by tightening the nut 33 with the washer 32 positioned against the internal end surface of the base plate.

A generally C-shaped brake member 34 is mounted in the tubular section 28 of the upper member U' by means of a pair of pins 35 and 36. The pin 35 passes through aligned circular apertures 28a in the tubular section 28, and through a circular aperture 34a in one arm of the brake member 34. The pin 36 passes though aligned elongate apertures 28b in the section 28, and though a circular aperture 34b in the other arm of the brake member 34. The brake member 34 is made of nylon 6,6, and is formed with an internal trapezoidal cross-section (acme) screw thread (not shown) which complements the external screw thread 23a of the screw 23. As with the embodiment of FIGS. 1 to 6, the brake members 23 and 34 constitute load-bearing means for pivotally connecting the upper and lower members U' and L'.

The brake member 34 is formed with an arcuate cut-out 34c adjacent to a curved surface 34d thereof that is remote from the free ends of the arms provided with the apertures 34a and 34b. An extension stop bumper 37, which is made of urethane rubber, is mounted on the pin 25 for sliding movement within the arcuate cut-out 34c. A threaded pin 38, which is associated with aligned apertures 34e and 34f in the arms of the brake member 34, is provided for adjusting the frictional force applied to the screw 23 in a manner described below.

An anti-rattle spring 39, which seats in an aperture 28c formed in the section 28 and abuts the free end of the upper arm of the brake member 34, is provided to bias the pin 36 against the posterior ends of the slots 28b, thereby eliminating play. A resilient band (not shown) stretches between the pins 25 and 35 to provide knee extension bias. This band helps to pivot the lower member L' relative to the upper member U' during leg extension movements.

The second form of prosthetic knee operates in basically the same manner as the first form, the brake mechanism merely being inverted so that the brake member 34 is carried by the upper member U', and the acme screw 23 is carried by the lower member L' (as opposed to the brake member 12 of the first form of prosthetic knee being carried by the lower member L and the acme screw 8 being carried by the upper member U). The main advantage of the second form of prosthetic knee is that it provides a good bent knee cosmesis, as the curved surface 34d is exposed to the anterior of the knee during flexion. The cosmetic effect could be further improved by the provision of a cosmetic covering over the anterior of the knee.

As with the first form of prosthetic knee, the internal acme screw thread of the brake member 34 is a sliding fit on the thread 23a when the second form of prosthetic knee is not under load. When the brake member 34 is loaded, the acme threads tend to move so as to jam their flanks together and lock the brake member to the screw 23. Although nylon 6,6 running in polished stainless steel produces very low static and dynamic friction, the angle of the interengaging flanks of the threads of the screw 23 and the brake member 34 produces a total reaction force which is much greater than the radial force on the screw, thereby achieving good resistance to torque (and hence good braking) with relatively low applied loads.

The second form of prosthetic knee is similar to the first form in the way in which locking occurs when the knee is subjected to an axial load. Hyper-extension forces are borne by the pin 25 which stops the brake member 34. The pin 36 then restrains the base plate 27, as the pin is driven to its limits in the slots 28b. Thus, the brake member 34 is forced into the disengaged position, a high bending movement being induced about the pin 25.

The second form of prosthetic knee does, however, have a number of advantages compared with the first form of prosthetic knee. Thus, the provision of the arcuate slot 34c in the brake member 34 results in the portion of the brake member between the arcuate slot and the curved surface 34d acting as a leaf spring. As the brake member 34 applies a braking force to the screw 23, this leaf spring stores energy which is used to assist in releasing the brake member from its grip on the screw when the brake member is unloaded.

Another advantage of the second form of knee is that the bumper 37 carried by the pin 25 can engage the lower ends of the arcuate slots 34c to provide a stop to limit relative pivotal movement between the upper member U' and the lower member L'.

Yet another advantage is that the pin 38 can be used to vary the frictional force applied by the brake member 34 to the screw 23. Thus, by tightening the pin 38, the arms of the brake member 34 are pre-tensioned towards one another, thereby increasing the frictional force applied by the brake member to the screw 23. This enables the second form of prosthetic knee to be adjusted to suit amputees of different body weights, and also to adjust to different operational requirements such as running or walking.

The second form of prosthetic knee also has the advantage of being less bulky than the first form. Moreover, the way in which the screw 23 is mounted in the lugs 22 by the torque arms 24 and the pin 25 serves to locate the pivoting parts of the second form of prosthetic knee in all planes, and to resist torque from the brake member 34.

Figure 9:
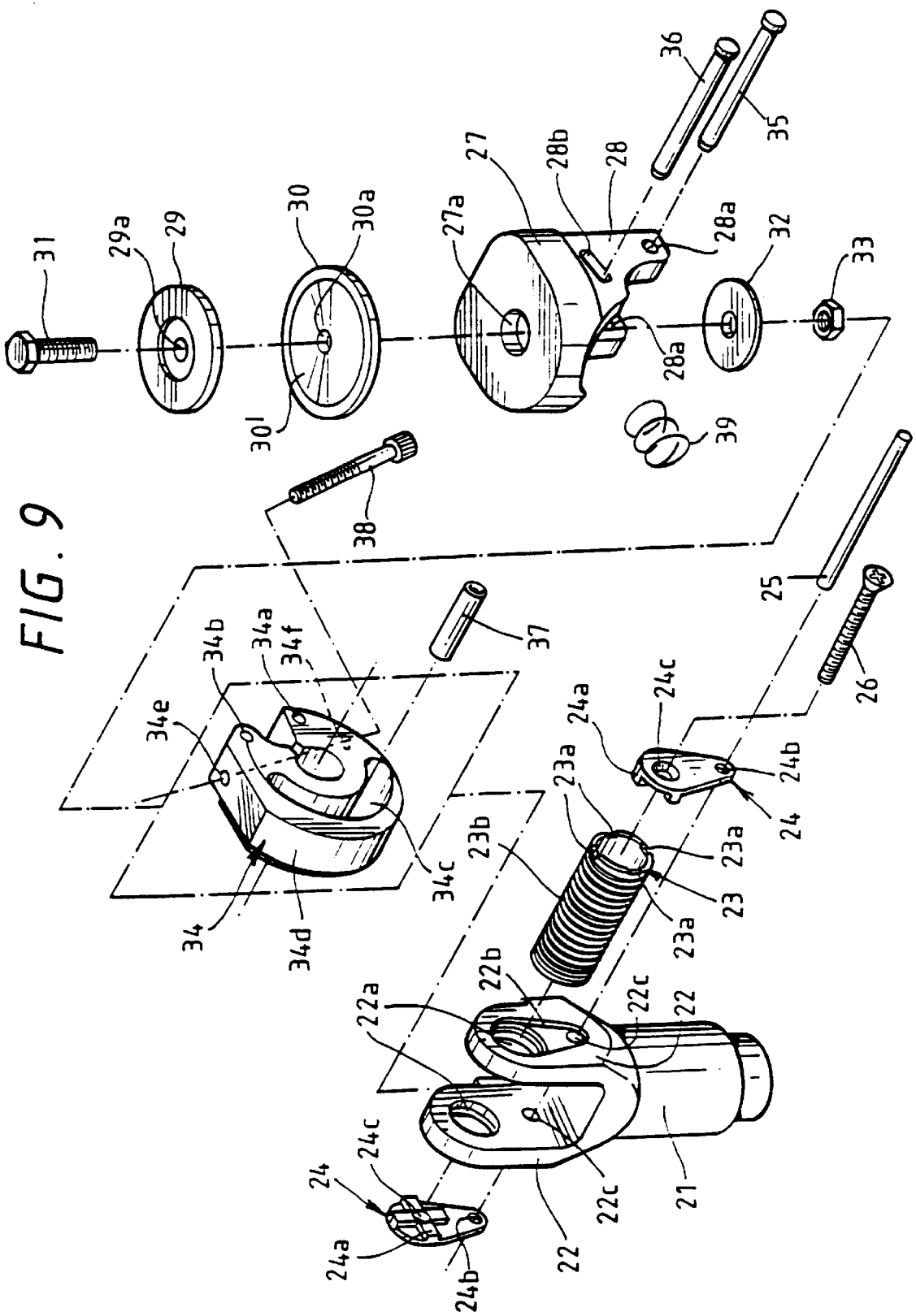
FIG. 9 is an exploded perspective view of the second form of prosthetic knee.
Figure 10:
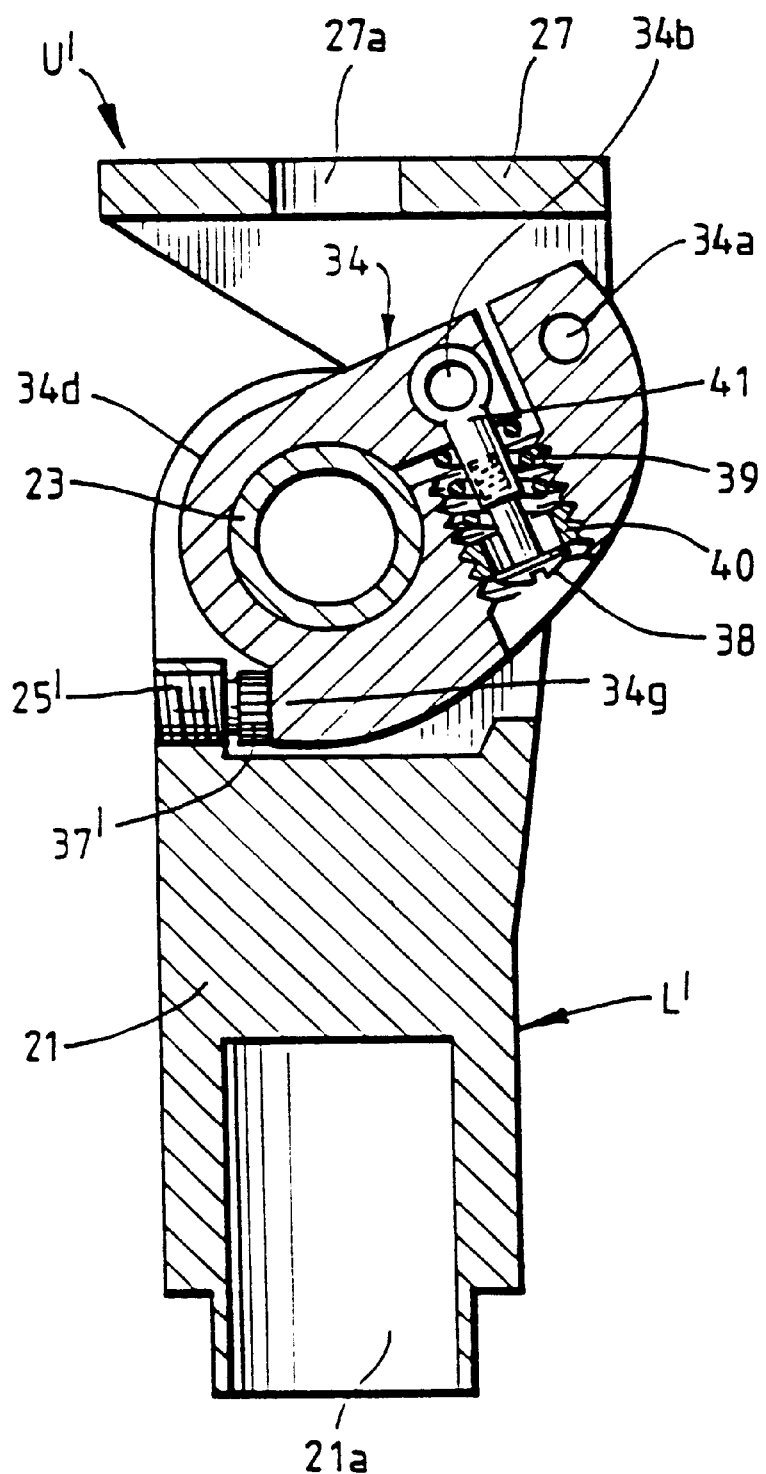
FIG. 10 is a longitudinal cross-section, similar to FIG. 8, of a third form of prosthetic knee constructed in accordance with the invention.
Figure 11:
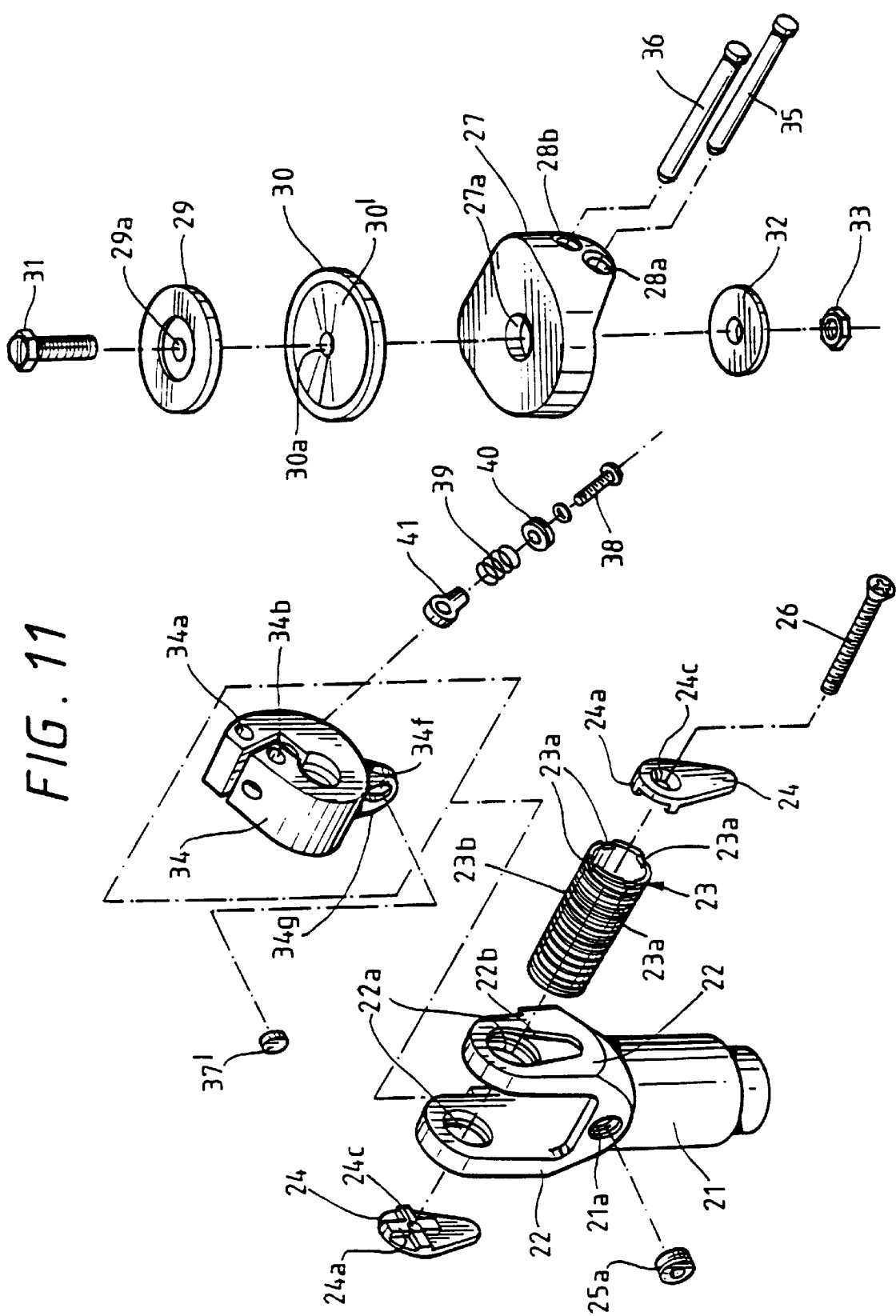
FIG. 11 is an exploded perspective view of the third form of prosthetic knee.
Figure 12:
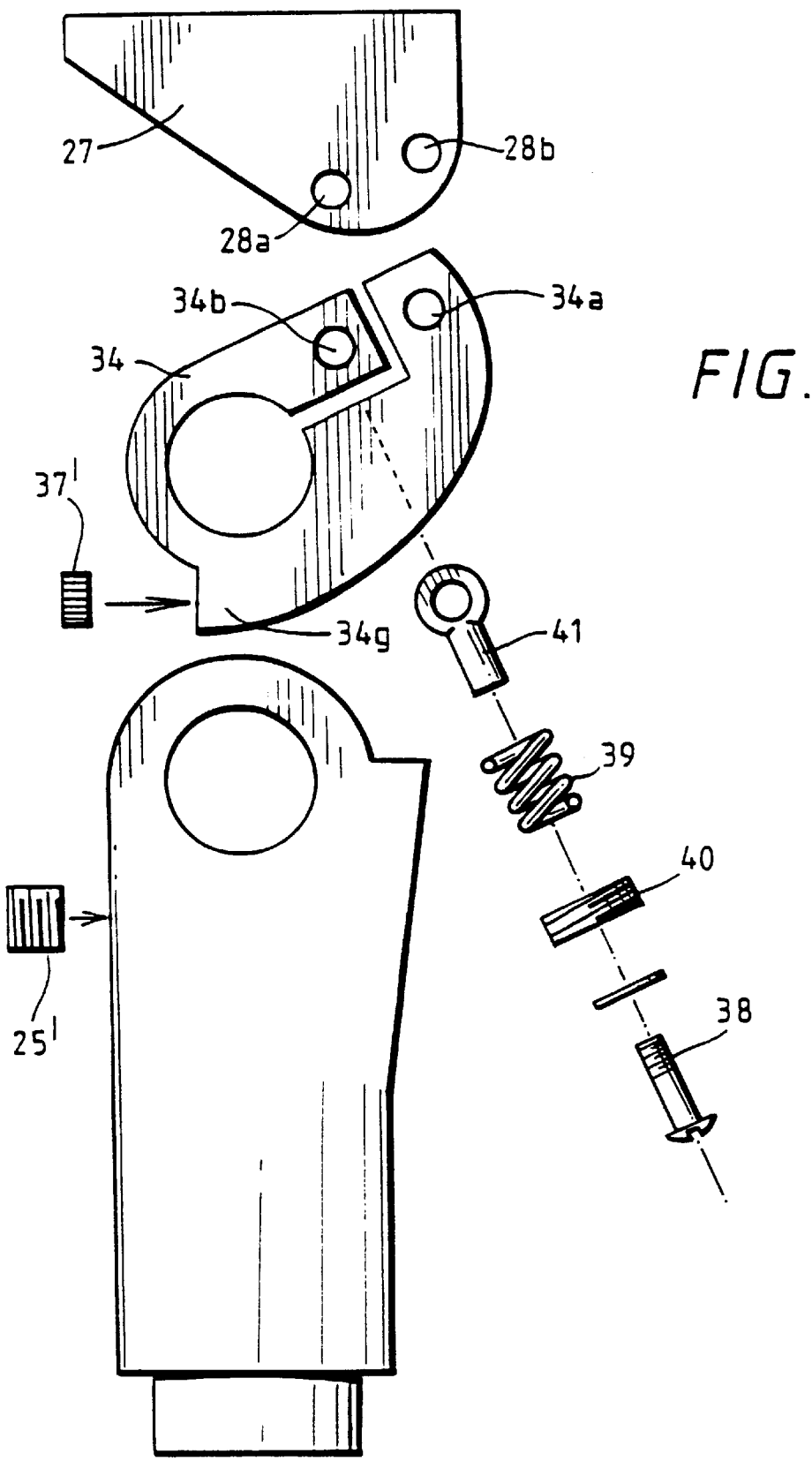
FIG. 12 is an exploded, schematic side elevation of the third form of prosthetic knee.

FIGS. 10 to 12 show a third form of prosthetic knee. This knee is a modified version of the knee of FIGS. 7 to 9, so like reference numerals will be used for like parts, and only the modifications will be described in detail.

Figure 8:
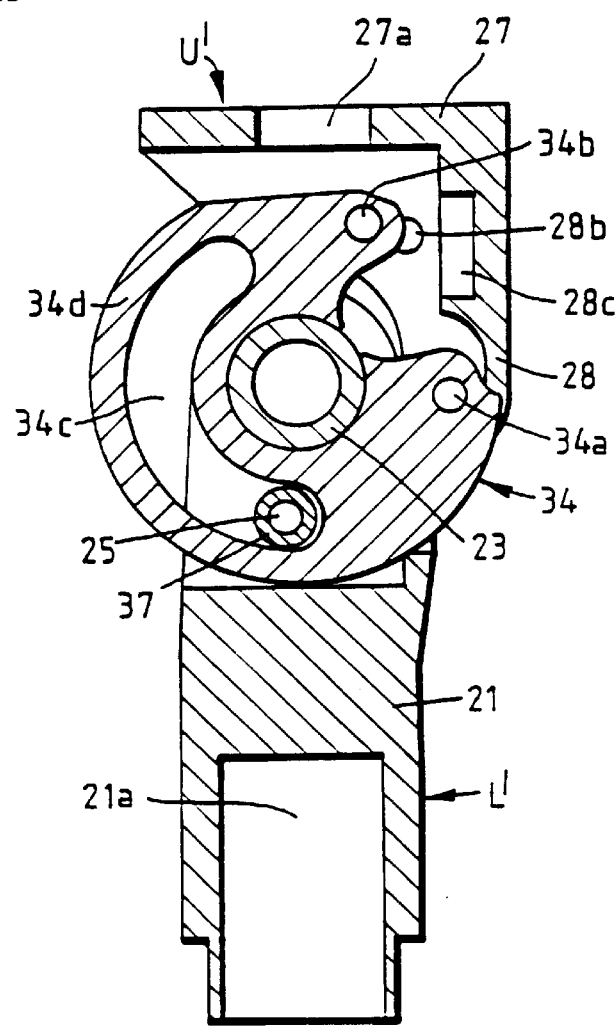
FIG. 8 is a cross-section taken on the line B—B of FIG. 7.

The lower knee member L', and the associated acme screw 23 and torque arms 24 are identical to those of FIGS. 7 to 9. This embodiment does not, however, include the pin 25, the extension stop bumper 37 and the arcuate slot 34c in the brake member 34. Instead, a hypertension stop 37' seated in a counter-bore 34f in the brake member 34 co-operates with an adjustable stop member 25' constituted by a screw mounted in a threaded bore 21b formed in the cup-shaped base 21.

The base plate 27 of the upper knee member U' of this embodiment has a modified shape compared with the corresponding member of FIGS. 7 to 9, the main difference being the re-positioning of the apertures 28a and 28b. Also, the aperture 28b is now a circular aperture.

The brake member 34 of FIGS. 10 to 12 is also a modified version of that of FIGS. 7 to 9. Thus, the brake member 34 of FIGS. 10 to 12 is generally D-shaped with a circular aperture at one end for receiving the acme screw 23. The counter-bore 34f previously mentioned is formed in a flange 34g at this end of the brake member 34.

The braking arrangement of FIGS. 10 to 12 is operated by rotating the two pins 35 and 36 about each other, these pins being roughly in line with the centreline of the axis of rotation of the knee members L' and U, that is to say with the axis of the acme screw 23. The rotation of the pins 35 and 36 about each other in the clockwise direction thus imparts a powerful mechanical "squeezing" of the screw 23, providing braking action.

In order to provide the necessary adjustability for the brake mechanism of FIGS. 10 to 12, a spring 39 (which is associated with the threaded pin 38) is used to hold the brake member 34 in a disengaged state when the knee mechanism is not weight bearing. A hollow adjusting screw 40 serves to pre-load the spring 39 appropriately for each user of the knee. This is especially important to ensure that the knee both brakes under weight bearing in every stride, and releases as weight is removed to allow free swing of the shin. The threaded pin 38 is attached to the pin 36 by means of a clevis 41, and bears on the adjusting screw 40 effectively preventing relative counter-clockwise rotation of the pins 35 and 36. Tightening of the threaded pin 38 then removes excessive clearance between the brake member 34 and the acme screw 23, and adds friction for swing control. The pin 38 thus prevents the brake member 34 from separating as hypertension loads rotate the pins 35 and 36 in the "loosen" (counter-clockwise) direction.

The artificial knees described above do not require the use of costly machined parts, instead using a standard acme screw and a moulded brake member. They are, therefore, cheaper to manufacture than known artificial knees. This cost advantage is enhanced by the reduction in the number of knee components needed resulting from using the brake components to pivot the two knee components together. They also have the advantage of providing a good locking action when loaded with axial loads, whilst ensuring good sliding between the brake components when the knee is not loaded. This good sliding property is enhanced by the self-lubricating qualities of nylon 6,6. In each case, the brake module (the screw 8 or 23 and the brake member 12 or 34) also serve as pivot bearings, thrust washers, end-play adjusters, and as the means for holding the knee together without the need for an additional load-bearing structure. Many of the parts of these knees are designed for low-cost replacement, and for simple servicing in the field. Where these knees are used without cosmetic coverings, their design is optimised to avoid pinch points and dirt traps.

It will be apparent that the artificial knees described above could be modified in a number of ways. For example, the screw 8 or 23 could have threads whose flanks are angled at other than the standard 29° of an acme screw. Indeed, it would be possible to replace the screw 8 or 23 by a member provided with one or more tapered rings. It would also be possible for the brake member 12 or 34 to be injection moulded around the screw 8 or 23 instead of forming its internal screw threads in a separate operation. It would also be possible to redesign the lower members L and L' to receive an H-section shin. The upper and lower member U, U' and L,L' may also be injection moulded members made of any other suitable plastics material.

What is claimed is:

1. An artificial knee comprising first and second pivotally interconnected knee components, and first and second interengaging brake components for locking the knee components together, the first and second brake components being associated respectively with the first and second knee components, wherein one of the brake components is made of a resiliently deformable material, and the arrangement is such that, when the artificial knee is subjected to a first load condition, the brake components are substantially free to slide against one another, and, when the artificial knee is under a second, higher load condition, said one brake component is resiliently deformed against the other brake component to lock the two brake components together, thereby locking the two knee components together, wherein the first and second brake components are provided with interengaging surfaces which are inclined to the axis about which the two knee components are pivoted, and the first and second brake components constitute the pivotal interconnection between the two knee components, the interengaging surfaces being configured so that side play of the knee components is prevented, the first brake component being an externally screw-threaded member, the flanks of the threads being inclined to the pivot axis, and the second brake component having a base portion and a pair of arms, the internal surface of the base portion being rounded and being provided with an internal screw thread which complements the external screw thread of the first brake component.

2. An artificial knee as claim in claim 1, wherein the free ends of the arms of the second brake component are connected to the second knee component by first and second pins.

3. An artificial knee as claimed in claim 2, wherein the second knee component defines a pair of spaced supports between which the second brake component is mounted, wherein the first pin passes through aligned circular apertures in the supports and through a circular aperture in one of the arms of the second brake component, and wherein the second pin passes through aligned apertures in the supports and through an aperture in the other arm of the second brake component.

4. An artificial knee as claimed in claim 3, wherein the second pin passes through aligned elongate apertures in the supports and through a circular apertures in said other arm.

5. A artificial knee as claimed in claim 4, wherein the apertures in the supports are so positioned that, when the artificial knee is subjected to the second load condition, the second pin is forced along the elongate apertures in the supports so that the internal screw threads of the rounded base portion of the second brake component are forced against the external screw threads of the first brake component, thereby locking the two brake components together.

6. An artificial knee as claimed in claim 4, wherein the circular aperture in said other arm of the second brake component is more remote from the second knee component than the circular aperture in said one arm of the second brake component.

7. An artificial knee as claimed in claim 6, wherein the free ends of the arms of the second brake component are directed towards the anterior of the knee.

8. An artificial knee as claimed in claim 3, wherein said other arm of the second brake component is tangential to the hyper-extension moment when the knee is a hyper-extension.

9. An artificial knee as claimed in claim 8, wherein the fulcrum of the hyper-extension moment is constituted by an abutment between portions of the two knee components, the abutment being anterior to the knee axis of rotation, and being on the side of said axis remote from the free end of said other arm of the second brake component.

10. An artificial knee as claim in claim 3, wherein the second pin passes through aligned circular apertures in the supports and through a circular aperture in said other arm.

11. An artificial knee as claimed in claim 10, wherein the apertures in the supports and the apertures in the arms of the second brake component are positioned such that the first and second pins are substantially aligned with the axis about which the two knee components are pivoted.

12. An artificial knee as claimed in claim 10, further comprising means for pre-tensioning the arms of the second brake component towards one another, the pre-tensioning means being constituted by a pin member associated with said one arm, an abutment member associated with said other arm, and a spring acting to bias the two arms apart, the pin member being fixed to the abutment member in such a manner as to permit relative movement therebetween.

13. An artificial knee as claimed in claim 12, wherein the free end of the pin member threadingly engages the abutment member.

14. An artificial knee as claim in claim 12, wherein the pin member is supported by an externally-threaded sleeve mounted in a threaded counter-born formed in said one arm.

15. An artificial knee as claimed in claim 14, wherein the spring acts between said other arm and the sleeve.

16. An artificial knee as claimed in claim 12, wherein the abutment member is a clevis having an apertured end through which the second pin passes, the engagement between the second pin and the clevis and the engagement of the second pin with the aperture in said other arm constituting means for fixing the abutment member to said other arm.

17. An artificial knee as claimed in claim 1, further comprising means for pre-tensioning the arms of the second brake component towards one another.

18. An artificial knee as claimed in claim 17, wherein a threaded pin constitutes the pre-tensioning means.

19. An artificial knee as claimed in claim 1, wherein the second brake component is a resilient deformable loop which can be tensioned around the first brake component by an actuating load.

20. An artificial knee as claimed in claim 1, wherein the second brake component is a generally V-shaped member, the base of the "V" constituting the base portion of the second brake component.

21. An artificial knee as claimed in claim 1, wherein the second brake component is a generally C-shaped member.

22. An artificial knee as claimed in claim 21, wherein the base portion of the C-shaped second brake component is formed with an arcuate slot.

23. An artificial knee as claim in claim 22, wherein the first knee component defines a pair of spaced support members between which the first brake component is mounted, the artificial knee further comprising a stop pin passing through aligned apertures in the support members and through the arcuate slot in the second brake component, the arrangement being such that pivotal movement between the two brake components is limited by engagement of the stop pin with the ends of the arcuate slot.

24. An artificial knee as claimed in claim 23, further comprising a tubular stop member positioned within the arcuate slot and closely surrounding the stop pin.

25. An artificial knee as claimed in claim 23, wherein the first brake component is separate from, and supported by, the first knee component; and the second brake component is separate from, and supported by, the second knee component, the rotation-preventing means being constituted by a pair of torque arms non-rotatably mounted in apertures formed in the support means, the torque arms being formed with inwardly-extending projections which mate with complementary slots formed in the adjacent ends of the first brake component.

26. An artificial knee as claimed in claim 25, wherein the rotation-preventing means further comprises a threaded pin for clamping the two torque arms firmly in their respective apertures.

27. An artificial knee as claimed in claim 1, wherein the second brake component is a generally D-shaped member, said one arm forming part of the upright of the D, and said other arm forming the curved part of the D.

28. An artificial knee comprising first and second pivotally interconnected knee components, and first and second interengaging brake components for locking the knee components together, the first and second brake components being associated respectively with the first and second knee components, wherein one of the brake components is made of a resiliently deformable material, and the arrangement is such that, when the artificial knee is subjected to a first load condition, the brake components are substantially free to slide against one another, and, when the artificial knee is under a second, higher load condition, said one brake component is resiliently deformed against the other brake component to lock the two brake components together, thereby locking the two knee components together, wherein the first and second brake components are provided with interengaging surfaces which are inclined to the axis about which the two knee components are pivoted, and the first and second brake components constitute the pivotal interconnection between the two knee components, the interengaging surfaces being configured so that side play of the knee components is prevented, the first brake component being an externally screw-threaded member, the flanks of the threads being inclined to the pivot axis, the first brake component being made of a generally rigid material such as stainless steel, the second brake component having a base portion and a pair of arms, the internal surface of the base portion being rounded and being provided with an internal screw thread which complements the external screw thread of the first brake component, the second brake component being said one brake component, and said resiliently deformable material being a plastics material.

29. An artificial knee as claimed in claim 28, wherein the resiliently deformable material is nylon 6.6.

30. An artificial knee comprising first and second pivotally interconnected knee components, and first and second interengaging brake components for locking the knee components together, the first and second brake components being associated respectively with the first and second knee components, wherein one of the brake components is made of a resiliently deformable material, and the arrangement is such that, when the artificial knee is subjected to a first load condition, the brake components are substantially free to slide against one another, and, when the artificial knee is under a second, higher load condition, said one brake component is resiliently deformed against the other brake component to lock the two brake components together, thereby locking the two knee components together, wherein the first and second brake components are provided with interengaging surfaces which are inclined to the axis about which the two knee components are pivoted, and the first and second brake components constitute the pivotal interconnection between the two knee components, one of said first and second brake components being made of a self-lubricating material, and the other of said brake components being made of a generally rigid material and being generally cylindrical with inclined surfaces for interengagement with complementary inclined surfaces of said one brake component, the inclined surfaces of said other brake component defining a plurality of wedge-shaped pockets along a generating line of the cylindrical surface of that component.

* * * * *